(12) United States Patent
Thompson et al.

(10) Patent No.: US 12,016,980 B2
(45) Date of Patent: *Jun. 25, 2024

(54) SCENT WARMER HAVING SLEEVE FOR REMOVABLY ATTACHING DECORATIVE BODY TO BASE AND RELATED METHODS

(71) Applicant: Scentsy, Inc., Meridian, ID (US)

(72) Inventors: R. Orville Thompson, Eagle, ID (US); Kyle Ostrem, Boise, ID (US); Mark Sullivan, Meridian, ID (US); Martin Stenger, Boise, ID (US)

(73) Assignee: Scentsy, Inc., Meridian, ID (US)

(*) Notice: Subject to any disclaimer, the term of this patent is extended or adjusted under 35 U.S.C. 154(b) by 0 days.

This patent is subject to a terminal disclaimer.

(21) Appl. No.: 18/312,236

(22) Filed: May 4, 2023

(65) Prior Publication Data

US 2023/0270909 A1    Aug. 31, 2023

Related U.S. Application Data

(63) Continuation of application No. 16/774,725, filed on Jan. 28, 2020, now Pat. No. 11,744,911.

(51) Int. Cl.
*A61L 9/03* (2006.01)
(52) U.S. Cl.
CPC ............. *A61L 9/03* (2013.01); *A61L 2209/13* (2013.01); *A61L 2209/15* (2013.01)
(58) Field of Classification Search
CPC ..... A61L 9/03; A61L 2209/13; A61L 2209/15
See application file for complete search history.

(56) References Cited

U.S. PATENT DOCUMENTS

| | | | |
|---|---|---|---|
| D641,858 S | 7/2011 | Thompson | |
| 8,412,029 B2 | 4/2013 | Browder et al. | |
| 8,772,675 B2 | 7/2014 | Juarez | |
| 8,809,744 B2 | 8/2014 | Stewart | |
| 8,878,102 B2 | 11/2014 | Juarez | |
| D721,449 S | 1/2015 | Chen | |
| D725,762 S | 3/2015 | Bishop | |
| 9,211,355 B2 | 12/2015 | Thompson et al. | |
| D807,485 S | 1/2018 | Bishop et al. | |
| D845,883 S | 4/2019 | Son | |
| D859,702 S | 9/2019 | Pattat | |
| 10,616,954 B2 * | 4/2020 | Belongia | H05B 3/26 |

(Continued)

OTHER PUBLICATIONS

Thompson et al., "Base for a Scent Warmer," Application for United States Design Patent via Electronic Filing, (Jan. 28, 2020), 10 pages.

*Primary Examiner* — Sean E Conley
*Assistant Examiner* — Brendan A Hensel
(74) *Attorney, Agent, or Firm* — TraskBritt

(57) ABSTRACT

An embodiment of the present disclosure may include a base for a scent warmer. The base may include a base member and a stem extending upwardly from the base member. The stem may be configured to carry a heating element thereon. The base may also include an elastomeric sleeve surrounding at least a portion of the stem. The elastomeric sleeve may be configured to apply a retention force between a removable decorative body and the stem. The elastomeric sleeve may include a wall member sized and configured to abut against the stem and a plurality of ribs extending radially outward from the wall member.

20 Claims, 5 Drawing Sheets

(56) References Cited

U.S. PATENT DOCUMENTS

| | | | |
|---|---|---|---|
| 2011/0110118 A1* | 5/2011 | Hsiao | F21S 8/035 362/249.02 |
| 2012/0024837 A1 | 2/2012 | Thompson | |
| 2012/0138594 A1 | 6/2012 | Stewart | |
| 2012/0318779 A1 | 12/2012 | Juarez | |
| 2012/0318780 A1 | 12/2012 | Juarez | |
| 2013/0020307 A1 | 1/2013 | Ashton et al. | |
| 2019/0328109 A1* | 10/2019 | Lin | A45D 40/04 |
| 2021/0106712 A1 | 4/2021 | Lee | |

* cited by examiner

SCENT WARMER HAVING SLEEVE FOR REMOVABLY ATTACHING DECORATIVE BODY TO BASE AND RELATED METHODS

CROSS-REFERENCE TO RELATED APPLICATION

This application is a continuation of U.S. patent application Ser. No. 16/774,725, filed Jan. 28, 2020, now U.S. Pat. No. 11,744,911, issued Sep. 5, 2023, the disclosure of which is hereby incorporated herein in its entirety by this reference.

TECHNICAL FIELD

Embodiments of the present disclosure relate generally to scent warmers for warming wax, oil, or other substances to produce a fragrance and methods of assembling scent warmers.

BACKGROUND

Scent warmers are configured to heat wax, oil, or other substances to produce a fragrance. Some scent warmers include a heating element such as an incandescent light bulb or a resistive heating element, a receptacle for the wax, oil, or other substances, and a body for retaining the receptacle relative to the heating element. In some scent warmers, the body may be decorative.

BRIEF SUMMARY

An embodiment of the present disclosure may include a base for a scent warmer. The base may include a base member and a stem extending upwardly from the base member. The stem may be configured to carry a heating element thereon. The base may also include an elastomeric sleeve surrounding at least a portion of the stem. The elastomeric sleeve may be configured to apply a retention force between a removable decorative body and the stem. The elastomeric sleeve may include a wall member sized and configured to abut against the stem and a plurality of ribs extending radially outward from the wall member.

Another embodiment of the present disclosure may include a method of securing together a removable decorative body and a base of a scent warmer. The method may include positioning an elastomeric sleeve on a stem extending upwardly from the base of the scent warmer such that the elastomeric sleeve surrounds at least a portion of the stem. The elastomeric sleeve may include a wall member sized and configured to abut against the stem and a plurality of ribs extending radially outward from the wall member. The method may also include positioning the removable decorative body around the elastomeric sleeve on the stem and deforming at least one of the plurality of ribs of the elastomeric sleeve. The elastomeric sleeve may apply a retention force between the removable decorative body and the stem.

BRIEF DESCRIPTION OF THE DRAWINGS

While the specification concludes with claims particularly pointing out and distinctly claiming that which is regarded as the present invention, various features and advantages of embodiments of the disclosure may be more readily ascertained from the following description of embodiments of the disclosure when read in conjunction with the accompanying drawings.

DETAILED DESCRIPTION

Figure 1:
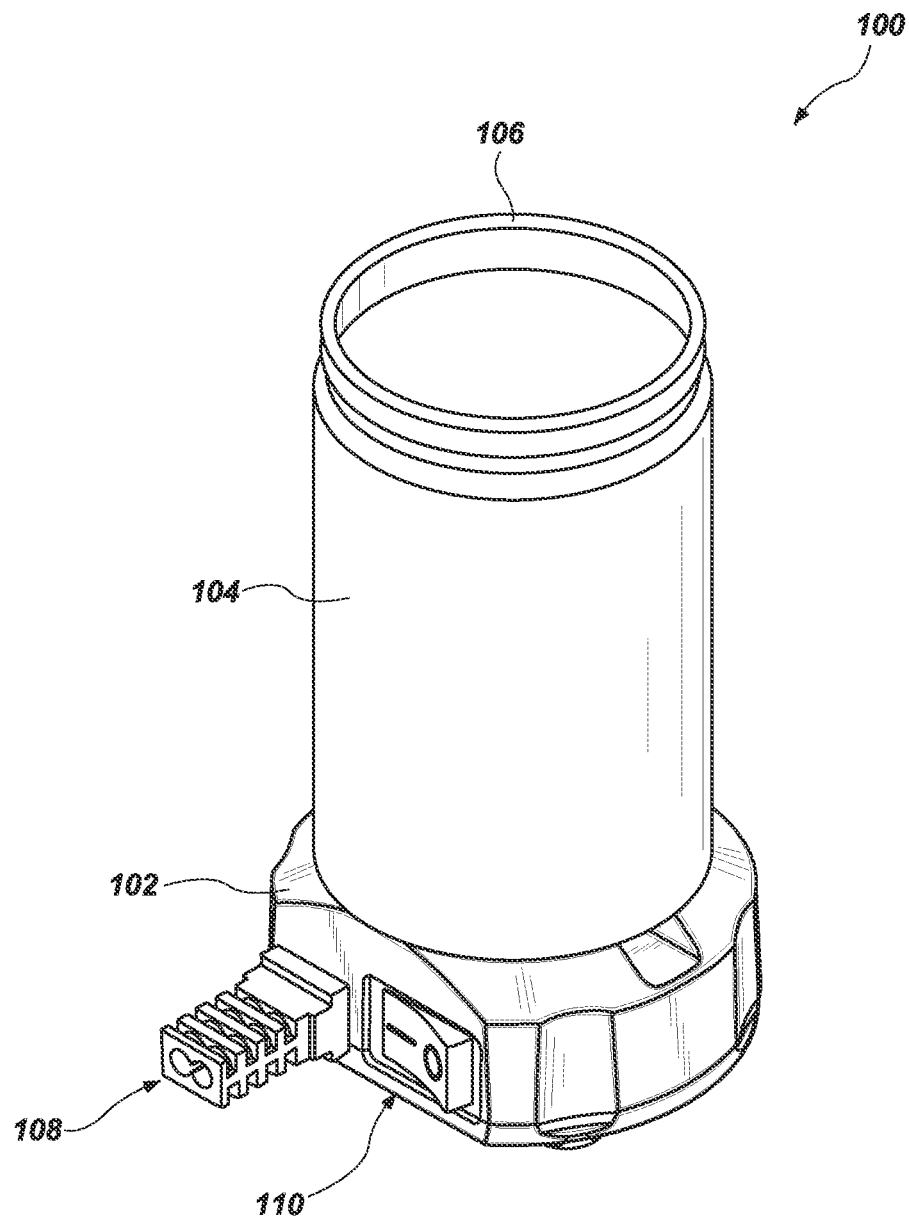
FIG. 1 illustrates a scent warmer having a base and a removable decorative body in accordance with one or more embodiments of the present disclosure.

The illustrations presented herein are not meant to be actual views of any particular scent warmer, component thereof, or method, but are merely representations which are employed to describe certain embodiments of the present disclosure. For clarity in description, various features and elements common among the illustrated embodiments may be referenced with the same or similar reference numerals.

As used herein, any directional term (e.g., up, upward, upper, lower, side, top, bottom, etc.) refers to a direction relative to the scent warmer when the scent warmer is used during normal operation. By way of non-limiting example, "upwardly from the base member" refers to a direction perpendicular to a surface (ostensibly a plane) on which the base member is placed in an orientation for use, and used to heat wax, oil, or other substances to produce a fragrance. As another non-limiting example, "top" refers to a portion of farther from the surface on which the base member is placed than another portion, which may be referred to as the "bottom."

As used herein, the terms "substantially" and "about" in reference to a given parameter, property, or condition means and includes to a degree that one of ordinary skill in the art would understand that the given parameter, property, or condition is met with a degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met. As a non-limiting examples, if a first length is given as twice as long as a second length, the first length may be twice as long as the second length plus or minus 10% of the second length.

As used herein, the term "and/or" includes any and all combinations of one or more of the associated listed items.

In some embodiments, a scent warmer may be configured to heat wax, oil, or other substances to produce a fragrance. The scent warmer may include a heating element, a receptacle for the wax, oil, or other substances, and a body retaining the receptacle in relation to the heating element. In some embodiments, the body may be decorative. For example, the heating element, in addition to producing heat, may produce light. The body may include transparent, translucent, and opaque portions in various colors that may variously allow light to pass through the body in a visually appealing way.

In some embodiments, the body may be removable. The body being removable allows for the body to be interchangeable with other bodies. The body being removable may also increase the ease of cleaning, maintaining, replacing parts (e.g., the heating element) of, and/or repairing the scent warmer and/or the body.

Embodiments of the present disclosure may relate to a base for a scent warmer that includes components that provide for removably attaching a removable decorative body to the base. In particular, some embodiments may include an elastomeric sleeve configured to surround a stem of the base and configured to be inserted into an opening of the removable decorative body. The elastomeric sleeve may be configured to apply a retention force between the removable decorative body and the stem of the base.

FIG. 1 illustrates a scent warmer 100 having a base and a removable decorative body 104 in accordance with one or more embodiments of the present disclosure. The scent warmer 100 may include a base member 102 and the removable decorative body 104. The base member 102 may include an electrical input 108 and an on/off switch 110. The removable decorative body 104 may include a warming dish 106.

The scent warmer 100 may be configured to heat wax, oil, or other substances to produce a fragrance. As such, the scent warmer 100 may include a heating element (not shown). The heating element may be attached to the base member 102 and may be positioned within the removable decorative body 104 when the removable decorative body 104 is positioned on top of and/or attached to the base member 102.

The base member 102 may be configured to receive electrical power at the electrical input 108. The base member 102 may supply the electrical power to the heating element which may produce heat. The on/off switch 110 may be configured to toggle power to the heating element. In particular, the on/off switch 110 may, when switched on, allow power to flow into the heating element thus allowing the heating element to heat. And when switched off, the on/off switch 110 may disconnect the heating element from power.

The removable decorative body 104 may include the warming dish 106 which may be a receptacle for wax, oil, or other substances. The removable decorative body 104 may retain the warming dish 106 relative to the heating element. Though illustrated at the top of the removable decorative body 104 the warming dish 106 may be located at a number of different locations relative to the warming dish 106. As a non-limiting example, the warming dish 106 may include a channel around a circumference of the removable decorative body 104.

The removable decorative body 104 may be configured to channel or direct heat from the heating element to the warming dish 106. For example, the removable decorative body 104 may be arranged to retain the warming dish 106 at a certain proximity to the heating element. Additionally, the removable decorative body 104 may include channels or vents for heat energy and/or air to move relative to the removable decorative body 104.

Additionally, the removable decorative body 104 may be decorative and/or include decorative elements. As non-limiting examples, the removable decorative body 104 may include shapes, colors, thicknesses, and/or degrees of translucency that may be intended to increase the visual appeal of the scent warmer 100. As a specific non-limiting example, the heating element may include an incandescent light bulb. The removable decorative body 104 may include various colors, thicknesses of material, and/or degrees of translucency designed to be visually appealing when the removable decorative body 104 is lit from within by the incandescent light bulb.

The base member 102 may be configured to be removably attached to the removable decorative body 104. Thus, the base member 102 may allow for replacement of the removable decorative body 104 with another removable decorative body. There are various means for removably attaching the removable decorative body 104 to the base member 102; the present disclosure will discuss several with regard to FIG. 2.

Figure 2:
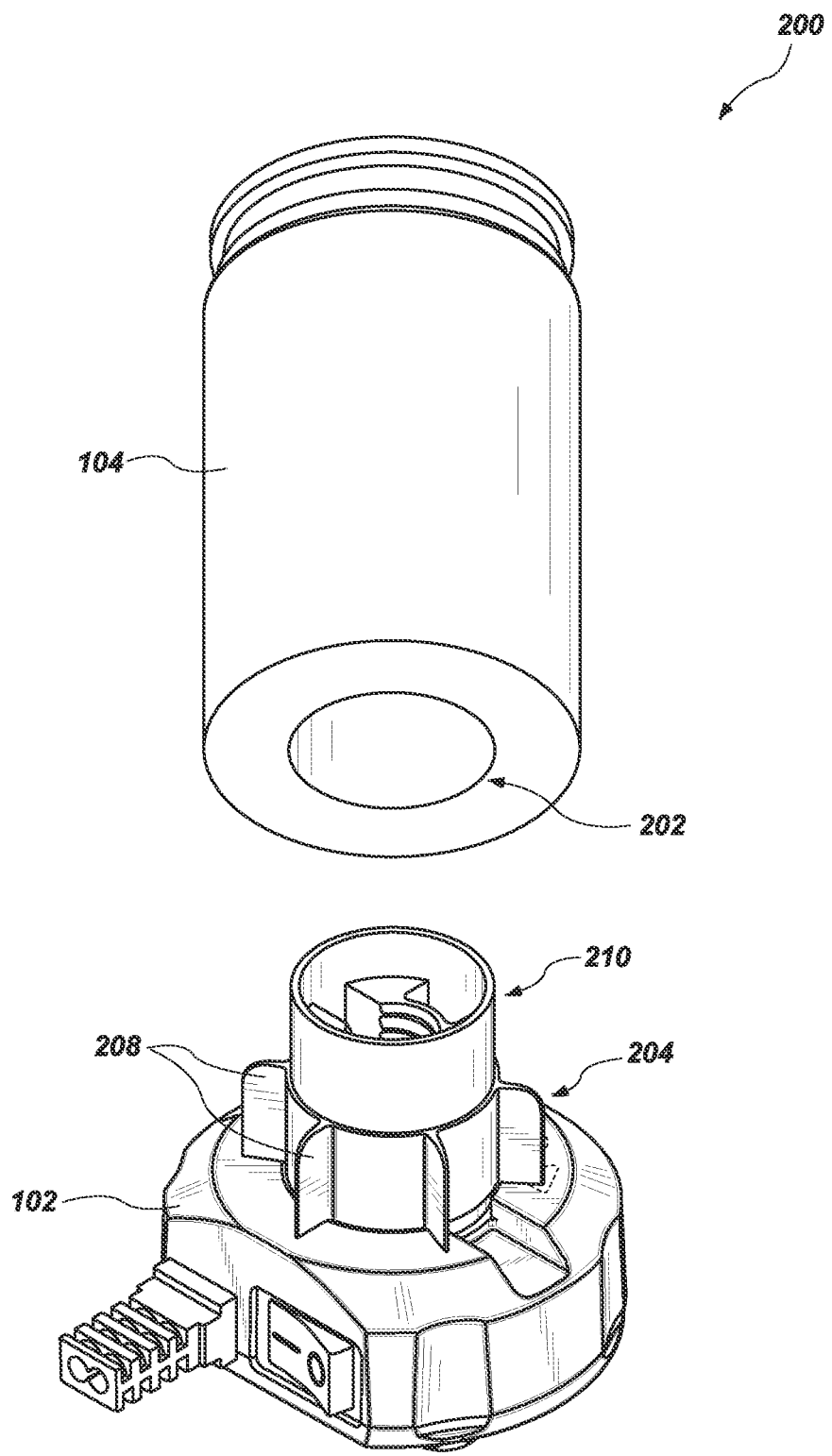
FIG. 2 is an exploded view of the scent warmer of FIG. 1, and illustrates an elastomeric sleeve that may be used to retain the removable decorative body on the base.

FIG. 2 is an exploded view of the scent warmer 100 of FIG. 1, and illustrates an elastomeric sleeve 204 that may be used to retain the removable decorative body 104 on the base in accordance with one or more embodiments of the present disclosure.

The removable decorative body 104 includes an opening 202. The opening 202 may be part of a removable decorative body 104. The opening 202 may define a void in the removable decorative body 104. The opening 202 may include a lip or flange defining the void in the removable decorative body 104. The opening 202 may include a height or thickness. The opening 202 may be sized and configured for removable attachment to the base member 102. As a non-limiting example, in FIG. 2, the opening 202 is circular. Embodiments of the present disclosure may include openings of other shapes, such as, for example, a hexagon, a square, or an oval, without limitation.

The base member 102 of the scent warmer 100 includes a stem 210 extending upward from the base member 102. In some embodiments, the stem 210 may be configured to carry a heating element (not shown) thereon. For example, the stem 210 may include a socket configured to receive an incandescent light bulb. Additionally or alternatively, the stem 210 may include a receptacle configured to receive a heating element that may include a resistive heating element that may or may be designed to produce light.

In some embodiments, the removable decorative body 104 may be positioned on the base member 102 with the stem 210 protruding through the opening 202 into the removable decorative body 104.

The scent warmer 100 and/or the base member 102 of the scent warmer 100 may include an elastomeric sleeve 204. The elastomeric sleeve 204 may be configured to apply a retention force between the removable decorative body 104 and the stem 210. As such, the elastomeric sleeve 204 may be configured to retain the removable decorative body 104 relative to the base member 102.

The elastomeric sleeve 204 may include a wall member 206 and multiple ribs 208. The ribs 208 may extend radially outward from the wall member 206. The wall member 206 may be configured to abut against and substantially surround the stem 210. Additional detail regarding the elastomeric sleeve 204, including the wall member 206 and the ribs 208 is given below with regard to FIGS. 3-5D.

The elastomeric sleeve 204 may be formed of an elastomeric material, for example, silicone or rubber. The elastomeric sleeve 204 may be deformable and may generate a restorative force in response to being deformed. The restorative force may be applied between the base member 102 and the removable decorative body 104 to apply a retentive force between the removable decorative body 104 and the stem 210.

As a non-limiting example, in some embodiments, a distance between tips of opposing ribs 208 may be greater than a diameter of the opening 202. As such, when the removable decorative body 104 is placed on the base member 102 and the stem 210, including the elastomeric sleeve 204, is placed in the opening 202, the opening 202 may deform the ribs 208. The opening 202 may deform the ribs 208 by pushing the ribs 208 inward radially or to a side. The ribs 208 may generate a restorative force, pushing radially outward against the opening 202. The restorative force of the ribs 208 pushing radially outward on the opening 202 of the removable decorative body 104 may work to retain the opening 202 relative to the stem 210 and thus, to retain the removable decorative body 104 relative to the base member 102. Additional detail regarding the deformation of the elastomeric sleeve 204 by the opening 202 is given below with regard to FIGS. 4A and 4B.

As another non-limiting example, in some embodiments, the inner diameter of the wall member 206 may be smaller than the outer diameter of the stem 210. Thus, when the elastomeric sleeve 204 is fitted around the stem 210, the elastomeric sleeve 204 may stretch radially outward and generate a restorative force pressing radially inward on the stem 210. The restorative force may retain the elastomeric sleeve 204 relative to the stem 210. In other embodiments, the inner diameter of the wall member 206 may be substantially the same size as or larger than the outer diameter of the stem 210.

As another non-limiting example, in some embodiments, the inner diameter of the wall member 206 may be substantially the same size as or larger than the outer diameter of the stem 210. In these or other embodiments, radially inward force of the opening 202 on the ribs 208 may deform the wall member 206 pressing the inner circumference of the wall member 206 against the stem 210. This inward pressing of the wall member 206 on the stem 210 may retain the elastomeric sleeve 204 relative to the stem 210.

In FIG. 2 the stem 210 and the elastomeric sleeve 204 are both illustrated as being round. In some embodiments, either or both of the stem 210 and the elastomeric sleeve 204 may be any suitable shape including, as non-limiting examples, round, triangular, square, pentagonal, hexagonal, heptagonal and octagonal. In these embodiments, the shape of the elastomeric sleeve 204 may be configured to relate to the shape of the stem 210. For example, the elastomeric sleeve 204 may be configured to such that it is the same shape as the stem 210. Alternatively, the elastomeric sleeve 204 may be configured to such that it is substantially the same size as, or smaller than, the stem 210 even if the elastomeric sleeve 204 is not the same shape as the stem 210.

Figure 3:
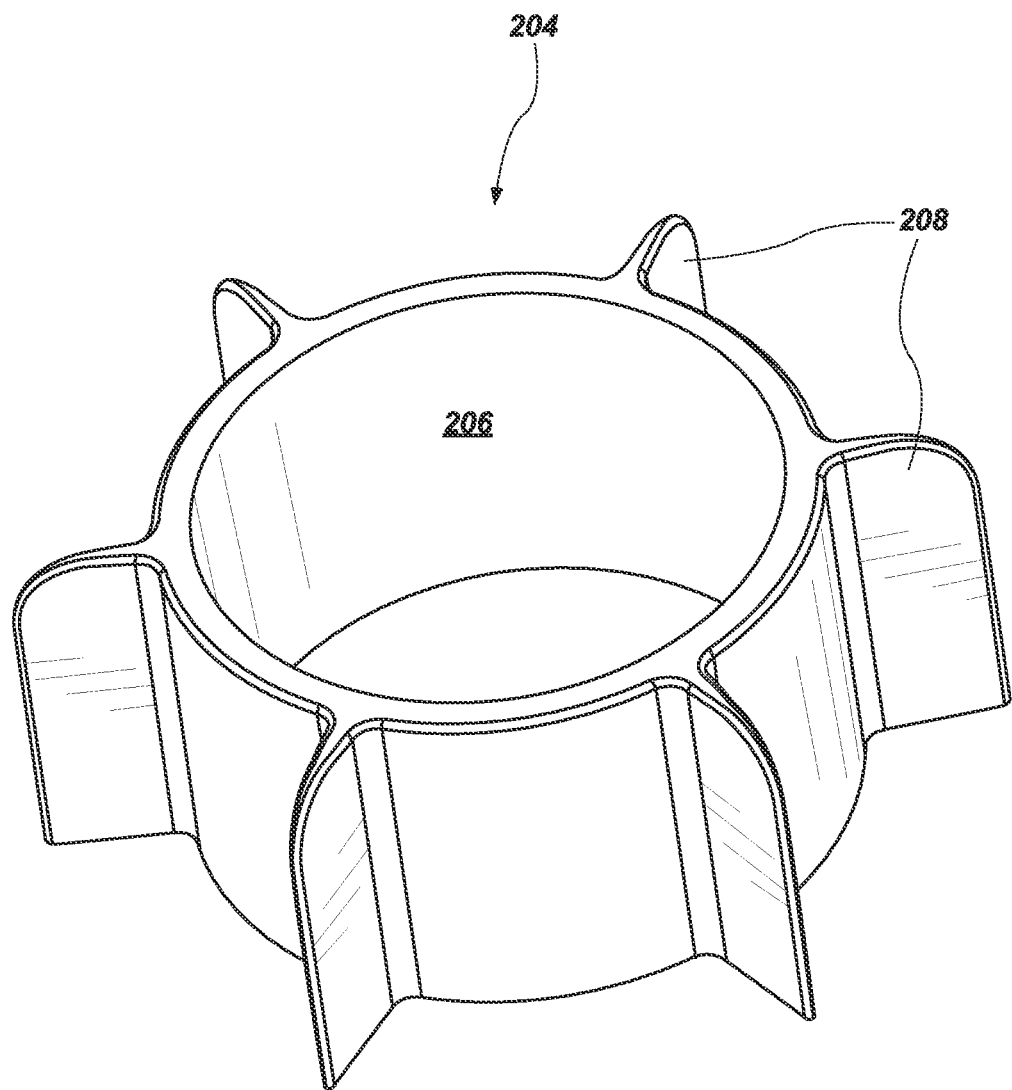
FIG. 3 illustrates the elastomeric sleeve of the scent warmer of FIG. 2, which may be used to retain the removable decorative body on the base in accordance with one or more embodiments of the present disclosure.

FIG. 3 illustrates the elastomeric sleeve 204 of FIG. 2, which may be used to retain the removable decorative body 104 of FIG. 2 on the stem 210 of FIG. 2 in accordance with one or more embodiments of the present disclosure. The elastomeric sleeve 204 includes a wall member 206 and ribs 208. Though the elastomeric sleeve 204 of FIG. 3 is illustrated with six ribs, embodiments of the present disclosure may include any suitable number of ribs, as non-limiting examples, the elastomeric sleeve may include three, four, five, seven, or eight ribs. Additionally, though the elastomeric sleeve 204 of FIG. 3 is illustrated having a hollow-cylindrically-shaped wall member 206 (i.e., round when viewed from the top), embodiments of the present disclosure may include a wall member of any suitable shape, as non-limiting examples, the wall member may be triangular, square, pentagonal, hexagonal, or heptagonal when viewed from the top.

In some embodiments, the elastomeric sleeve 204 may include a beveled edge. The beveled edge may be configured to be at the top of the elastomeric sleeve 204 when the elastomeric sleeve 204 is positioned on the base member 102. Additionally, in some embodiments, the ribs 208 include a rounded edge. The rounded edge may be configured to be at the top of the elastomeric sleeve 204 when the elastomeric sleeve 204 is positioned on the base member 102. The beveled top edge and/or the rounded edge may make it easier to place the opening 202 of the removable decorative body 104 over the elastomeric sleeve 204. Additional detail regarding features of the elastomeric sleeve 204 are given below with regard to FIG. 5.

Figure 4B:
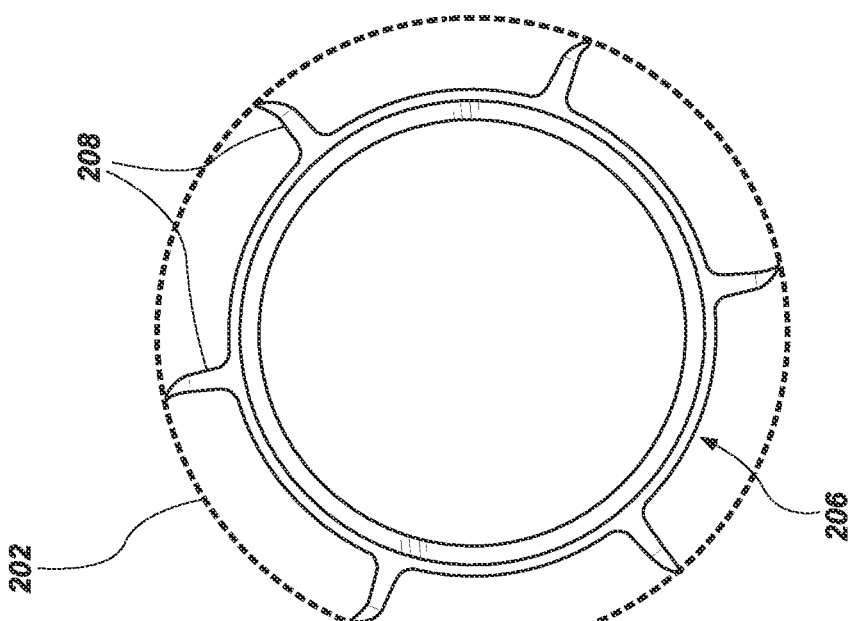
FIG. 4B illustrates the elastomeric sleeve of FIG. 3 with ribs of the elastomeric sleeve deformed to fit into the opening of the removable decorative body.
Figure 4A:
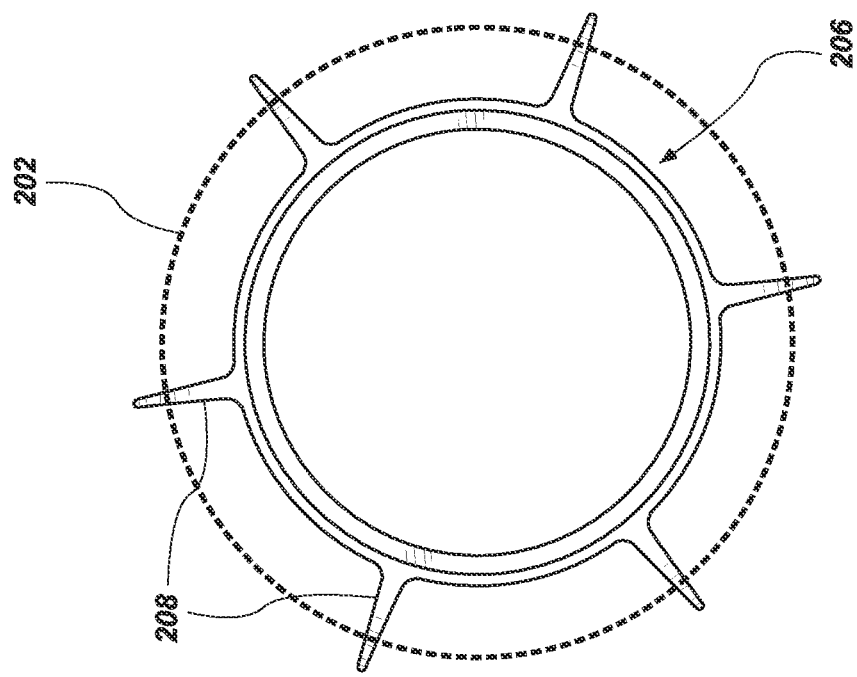
FIG. 4A illustrates the elastomeric sleeve of FIG. 3 in relation to a size of an opening of a removable decorative body.

FIG. 4A illustrates the elastomeric sleeve 204 of FIG. 3 in relation to a size of an opening 202 of a removable decorative body 104. FIG. 4B illustrates the elastomeric sleeve 204 of FIG. 3 with ribs 208 of the elastomeric sleeve 204 deformed to fit into the opening 202 of the removable decorative body 104.

FIGS. 4A and 4B illustrate the size of the opening 202 as a circle. For descriptive and illustrative purposes, the removable decorative body 104 is omitted and the opening 202 is illustrated as a circle.

FIG. 4B illustrates deformation of the ribs 208 by the opening 202. In particular, FIG. 4B illustrates the results of positioning a removable decorative body 104 including a circular opening 202 onto an elastomeric sleeve 204. More specifically, FIG. 5 illustrates the case in which the opening 202 has an inner diameter smaller than the distance between the tips of two opposing ribs 208. In such a case, the opening 202 deforms the ribs 208.

As described above, the ribs 208 may be formed of an elastomeric material that may exert a restorative force when deformed. As such, the ribs 208 may exert a radially outward force on the opening 202. The radially outward force of the ribs 208 on the opening 202 may be a retention force, retaining the opening 202 relative to the elastomeric sleeve 204 and/or the stem 210.

In some embodiments, the retention force may be greater than the weight of either the removable decorative body 104 or the base member 102. In these or other embodiments, it may require force greater than the weight of the removable decorative body 104 to assemble the removable decorative body 104 on the base member. When assembled, the removable decorative body 104 may be retained relative to the base member 102 such that the removable decorative body 104 does not slide downward toward the base member 102 unless additional force is exerted between the removable decorative body 104 and the base member 102. It may be possible for a person to lift the scent warmer 100 by pulling upward on the removable decorative body 104 without the base member 102 falling from the bottom of the decorative body 104. Further, to remove the removable decorative body 104 from the base member 102, a person may need to pull upward on the removable decorative body 104 while retaining, or pushing downward on the base member 102.

As described above, in some embodiments, the opening 202 may be a shape other than circular. In such cases, the opening 202 and the elastomeric sleeve 204 may be configured such that a distance between tips of opposing ribs may be greater than a hypothetical line passing through the center of the opening 202 and bisecting the opening 202.

As described above, in some embodiments, the elastomeric sleeve 204 may include an odd number of ribs. In such cases, the opening 202 and the elastomeric sleeve 204 may be configured such that a circle defined by the tips of all of the ribs may be larger than the opening 202.

FIGS. 5A-5D illustrate different views of an elastomeric sleeve 204 in accordance with one or more embodiments of the present disclosure. The elastomeric sleeve 204 of FIGS. 5A-5D includes a wall member 206 and six evenly-radially-spaced ribs 208. This description of FIGS. 5A-5D includes numerical measurements of features of the elastomeric sleeve 204; these are non-limiting examples of suitable dimensions of the features of an elastomeric sleeve.

Figure 5C:
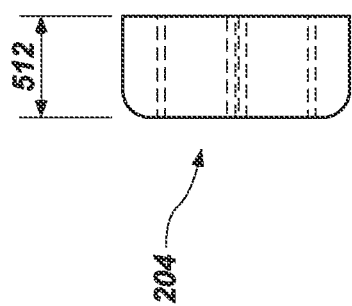
FIG. 5C is a side view of the elastomeric sleeve of FIGS. 5A-5B.
Figure 5A:
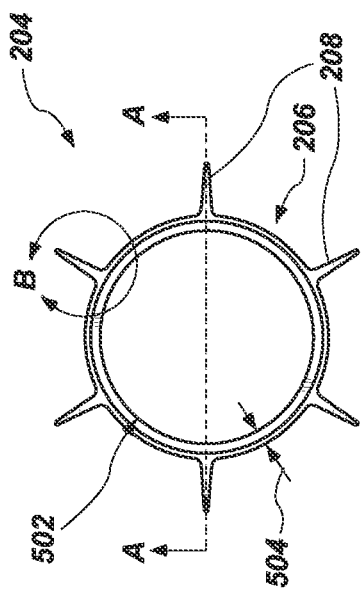
FIG. 5A is a top view of an elastomeric sleeve of FIG. 3.

FIG. 5A is a top view of an elastomeric sleeve of FIG. 3. FIG. 5A illustrates an inner diameter 502 of the wall member 206. The inner diameter 502 may be 24 millimeters (mm). The inner diameter 502 may have a tolerance of plus or minus 0.08 mm. FIG. 5A illustrates a radial thickness 504 of the wall member 206. The radial thickness 504 may be 1.5 mm with a tolerance of plus or minus 0.15 mm. Thus, according to the example dimensions described with regard to FIGS. 5A-5D, the radial thickness 504 may be about one sixteenth the inner diameter 502. In these or other embodiments, the radial thickness may be between about 4% and about 12% of an inner diameter of the wall member.

Figure 5B:
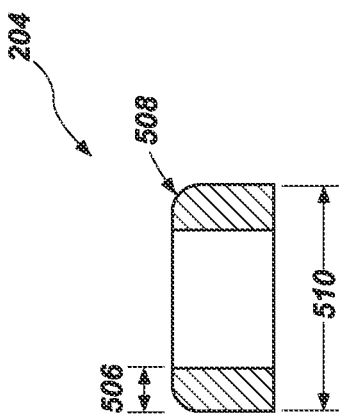
FIG. 5B is a cross-sectional view of the elastomeric sleeve of FIG. 5A as seen along section line A-A shown therein.

FIG. 5B is a cross-sectional view of the elastomeric sleeve of FIG. 5A as seen along section line A-A shown therein. FIG. 5B illustrates a cross-sectional length 510 of the elastomeric sleeve 204 across the sectional line A-A illustrated in FIG. 5A. The cross-sectional length 510 may be 39 mm. As such, according to the example dimensions described with regard to FIGS. 5A-5D, a rib length 506 of each of the ribs 208 may be, from the outer diameter of the wall member 206 to the tip of the rib, may be 6 mm. Thus, in some embodiments, the rib length 506 may be about one quarter the inner diameter 502. In these or other embodiments, the ribs length 506 may be between about 10% and about 40% of the inner diameter 502. Also, the rib length 506 of each rib, from the outer diameter of the wall member 206 to the tip of the rib, may be about three to five times the radial thickness 504.

FIG. 5B illustrates ribs 208 having a rounded edge 508. In some embodiments, each of the ribs 208 may have a rounded edge 508. The rounded edge 508 may be configured to be on the top side when the elastomeric sleeve 204 is placed on a stem 210. The rounded edges 508 may make it easier to place the opening 202 around the elastomeric sleeve 204. The radius of curvature of the rounded edge 508 may be about 3.3 mm.

FIG. 5C is a side view of the elastomeric sleeve of FIGS. 5A-5B. FIG. 5C the height 512 of the elastomeric sleeve 204 may be 15 mm, with a tolerance of 0.15 mm. As such, according to the example dimensions described with regard to FIGS. 5A-5D, the height 512 may be about five eighths the inner diameter 502. In these or other embodiments, height 512 may be between about 50% and about 75% of the inner diameter 502. In some embodiments, the height of each of the ribs 208 may be the same as the height 512 of the wall member 206. In other embodiments, the ribs 208 may be shorter than the wall member 206.

Figure 5D:
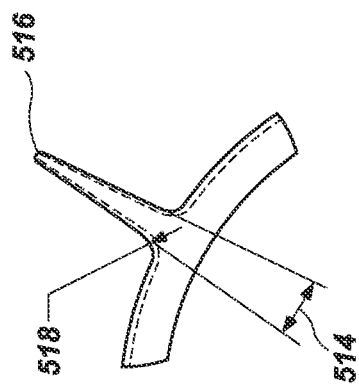
FIG. 5D is a partial top view of a portion of the elastomeric sleeve of FIGS. 5A-5C.

FIG. 5D is a partial top view of a portion of the elastomeric sleeve of FIGS. 5A-5C. FIG. 5D illustrates a section B of the elastomeric sleeve 204 illustrated in FIG. 5A. FIG. 5D illustrates a rib 208 having a two sidewalls and a rib tip 516.

Each of the ribs 208 may be thicker closer to the wall member 206 than at a point closer to the tip of the rib. In other words, the ribs 208 may narrow as they progress from the wall member 206 to their tips. There may be an angle 514 between the two sidewalls of each of the ribs 208. The angle 514 may be of between five and ten degrees. As a specific non-limiting example, the angle 514 between the two sidewalls of each of the ribs 208 may be 8.6 degrees. In some embodiments, the ribs 208, at their respective thickest points, e.g., where the ribs 208 meet the wall member 206, may be between about 50% and 150% of the radial thickness 504. In these or other embodiments, the ribs 208 may be four to five times longer than they are thick, at their respective thickest points.

Additionally, FIG. 5D illustrates a rib tip 516 that is rounded, e.g., the rib tip 516 may have radius of curvature of about 0.3 mm. And, FIG. 5D illustrates a rib-wall member interface 518 where the rib 208 meets the wall member 206. The rib-wall member interface 518 may be rounded, e.g., the rib-wall member interface 518 may have a radius of curvature of about 1 mm.

Also, the beveled edge of the elastomeric sleeve 204 is illustrated in FIG. 5D by the dashed lines. The wall member 206 and the ribs 208 may both include the beveled edge. As can be seen in FIG. 5D, the outer edge of the wall member 206 may be beveled. The inner edge of the wall member 206 may or may not be beveled.

While the present invention has been described herein with respect to certain embodiments, those of ordinary skill in the art will recognize and appreciate that it is not so limited. Rather, many additions, deletions, and modifications to the embodiments depicted and described herein may be made without departing from the scope of the invention as hereinafter claimed, and legal equivalents. In addition, features from one embodiment may be combined with features of another embodiment while still being encompassed within the scope of the invention as contemplated by the inventor. Further, the invention has utility in diffusers having different designs and configurations than those shown and described herein.

What is claimed is:

1. A scent warmer, comprising:
   a base member;
   a stem extending upwardly from the base member and configured to carry a heating element thereon; and
   an elastomeric sleeve surrounding at least a portion of the stem, the elastomeric sleeve configured to apply a retention force between a removable decorative body and the stem, the elastomeric sleeve comprising:
   a wall member sized and configured to abut against the stem; and
   ribs extending radially outward from the wall member, wherein the ribs narrow as they extend from the wall member to their tips.

2. The scent warmer of claim 1, wherein the ribs are deformable and are configured to exert the retention force when the ribs are deformed by being placed in an opening of the removable decorative body.

3. The scent warmer of claim 2, further comprising the removable decorative body, and wherein the removable decorative body defines an opening, and the ribs and the opening are configured such that when the ribs are placed in the opening, the opening deforms the ribs.

4. The scent warmer of claim 3, wherein tips of the ribs define a circle larger than the opening of the removable decorative body.

5. The scent warmer of claim 1, wherein the ribs are evenly spaced around the wall member.

6. The scent warmer of claim 1, wherein each of the ribs has a first thickness, measured in a circumferential direction, adjacent to the wall member and a second smaller thickness, measured in a circumferential direction, at a tip of the rib.

7. The scent warmer of claim 6, wherein an angle between a first sidewall of the rib and a second sidewall of the rib is between five and fifteen degrees.

8. The scent warmer of claim 6, wherein the first thickness is between about 50% and about 150% of a radial thickness of the wall member.

9. A scent warmer, comprising:
a base member;
a stem extending upwardly from the base member and configured to carry a heating element thereon; and
an elastomeric sleeve surrounding at least a portion of the stem, the elastomeric sleeve configured to apply a retention force between a removable decorative body and the stem, the elastomeric sleeve including a top side, the elastomeric sleeve comprising:
 a wall member sized and configured to abut against the stem;
 ribs extending radially outward from the wall member; and
 wherein a top surface of the wall member is coplanar with respective top surfaces of the ribs and wherein a bottom surface of the wall member is coplanar with respective bottom surfaces of the ribs.

10. The scent warmer of claim 9, wherein each of the ribs is substantially flat, in a height direction, and each of the ribs includes a rounded top edge.

11. The scent warmer of claim 9, wherein each of the ribs extends radially from the wall member by a distance that is between about 10% and about 40% of an inner diameter of the wall member.

12. The scent warmer of claim 9, wherein the stem comprises a cylinder and the wall member comprises a smooth hollow cylinder, without threads, sized and configured to surround the stem.

13. The scent warmer of claim 12, wherein an inner diameter of the wall member is the same size as or smaller than an outer diameter of the stem.

14. The scent warmer of claim 9, wherein there are six ribs spaced evenly, radially on the wall member.

15. The scent warmer of claim 9, wherein a radial thickness of the wall member is between about 4% and about 12% of an inner diameter of the wall member.

16. The scent warmer of claim 9, wherein a height of the wall member is between about 50% and about 75% of an inner diameter of the wall member.

17. The scent warmer of claim 9, further comprising the removable decorative body, and wherein the removable decorative body is configured to substantially surround the heating element.

18. An elastomeric sleeve to removably attach a decorative body to a heat-element-carrying stem of a base member of a scent warmer, the elastomeric sleeve comprising:
a wall member sized and configured to surround the heat-element-carrying stem; and
ribs extending radially outward from the wall member to exert a retention force against the decorative body when the ribs are placed in an opening of the decorative body when the decorative body is removably attached to the base member; wherein each of the ribs has a first thickness, measured in a circumferential direction, adjacent to the wall member and a second smaller thickness, measured in a circumferential direction, at a tip of the rib.

19. The elastomeric sleeve of claim 18, wherein an inner diameter of the wall member is the same size as or smaller than an outer diameter of the heat-element-carrying stem to retain the elastomeric sleeve relative to the heat-element-carrying stem when the wall member surrounds the heat-element-carrying stem.

20. The elastomeric sleeve of claim 18, wherein an inner diameter of the wall member is the same size as or larger than an outer diameter of the heat-element-carrying stem such that the when the ribs are placed in an opening of the decorative body the wall member is deformed and pressed against the heat-element-carrying stem to retain the elastomeric sleeve relative to the heat-element-carrying stem.

\* \* \* \* \*